(12) United States Patent
Pianca et al.

(10) Patent No.: US 8,359,107 B2
(45) Date of Patent: Jan. 22, 2013

(54) ELECTRODE DESIGN FOR LEADS OF IMPLANTABLE ELECTRIC STIMULATION SYSTEMS AND METHODS OF MAKING AND USING

(75) Inventors: Anne Margaret Pianca, Santa Monica, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 552 days.

(21) Appl. No.: 12/568,428

(22) Filed: Sep. 28, 2009

(65) Prior Publication Data

US 2010/0094387 A1    Apr. 15, 2010

Related U.S. Application Data

(60) Provisional application No. 61/103,996, filed on Oct. 9, 2008.

(51) Int. Cl.
*A61N 1/05* (2006.01)
(52) U.S. Cl. ...................................... 607/116
(58) Field of Classification Search ................. 607/115, 607/116
See application file for complete search history.

(56) References Cited

U.S. PATENT DOCUMENTS

| 5,000,194 | A | 3/1991 | van den Honert et al. |
| 5,036,862 | A | 8/1991 | Pohndorf |
| 5,330,525 | A | 7/1994 | Proctor |
| 5,344,439 | A | 9/1994 | Otten |
| 5,824,032 | A | 10/1998 | Belden |
| 5,843,148 | A | 12/1998 | Gijsbers et al. |
| 5,865,842 | A | 2/1999 | Knuth et al. |
| 5,865,843 | A | 2/1999 | Baudino |
| 5,957,965 | A | 9/1999 | Moumane et al. |
| 6,104,960 | A | 8/2000 | Duysens et al. |
| 6,181,969 | B1 | 1/2001 | Gord |
| 6,192,279 | B1 * | 2/2001 | Barreras et al. ............... 607/117 |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,047,084 | B2 * | 5/2006 | Erickson et al. ............... 607/116 |
| 7,107,097 | B2 | 9/2006 | Stern et al. |

(Continued)

FOREIGN PATENT DOCUMENTS

EP    0 862 925 B1    9/1998

(Continued)

OTHER PUBLICATIONS

U.S. Appl. No. 11/238,240, filed Sep. 29, 2005, 19 pages.

*Primary Examiner* — Brian T Gedeon
(74) *Attorney, Agent, or Firm* — Frommer Lawrence & Haug; Patrick R. Turner

(57) ABSTRACT

A lead includes a lead body with a distal end and a proximal end. A plurality of terminals are disposed at the proximal end of the lead body. A plurality of electrodes are disposed at the distal end of the lead body. Each electrode includes an electrode body and at least one anchoring member. The at least one anchoring member couples to the electrode body and extends into the lead body and beneath the electrode body to anchor the electrode to the lead body. A plurality of conductive wires electrically couple the plurality of electrodes to the plurality of terminals.

20 Claims, 9 Drawing Sheets

U.S. PATENT DOCUMENTS

| | | |
|---|---|---|
| 7,184,842 B2 | 2/2007 | Seifert et al. |
| 7,187,982 B2 | 3/2007 | Seifert et al. |
| 7,244,150 B1 | 7/2007 | Brase et al. |
| 7,418,298 B2 | 8/2008 | Shiroff et al. |
| 7,447,546 B2 | 11/2008 | Kim et al. |
| 7,463,934 B2 | 12/2008 | Tronnes et al. |
| 7,499,757 B2 | 3/2009 | Coe et al. |
| 7,765,011 B2 * | 7/2010 | Skubitz et al. ............... 607/115 |
| 2002/0042642 A1 | 4/2002 | Gerber |
| 2003/0109778 A1 | 6/2003 | Rashidi |
| 2003/0114905 A1 | 6/2003 | Kuzma |
| 2003/0195600 A1 | 10/2003 | Tronnes et al. |
| 2004/0024427 A1 | 2/2004 | Imran et al. |
| 2004/0059392 A1 | 3/2004 | Parramon et al. |
| 2004/0116977 A1 | 6/2004 | Finch et al. |
| 2005/0033394 A1 | 2/2005 | Seifert et al. |
| 2005/0033395 A1 | 2/2005 | Seifert et al. |
| 2005/0165465 A1 | 7/2005 | Pianca et al. |
| 2006/0004430 A1 | 1/2006 | Rossing et al. |
| 2007/0078455 A1 | 4/2007 | Rashidi |
| 2007/0150007 A1 | 6/2007 | Anderson et al. |
| 2007/0150036 A1 * | 6/2007 | Anderson ..................... 607/116 |
| 2007/0219595 A1 | 9/2007 | He |
| 2007/0239243 A1 | 10/2007 | Moffitt et al. |
| 2007/0255379 A1 | 11/2007 | Williams et al. |
| 2007/0288077 A1 | 12/2007 | Bulkes et al. |
| 2008/0071320 A1 | 3/2008 | Brase |
| 2008/0140168 A1 | 6/2008 | Walter et al. |
| 2008/0154349 A1 | 6/2008 | Rossing et al. |
| 2008/0183257 A1 | 7/2008 | Imran et al. |
| 2008/0188917 A1 | 8/2008 | Gerber et al. |
| 2008/0243220 A1 | 10/2008 | Barker |
| 2009/0012592 A1 | 1/2009 | Buysman et al. |
| 2009/0030331 A1 | 1/2009 | Hochareon et al. |
| 2009/0118804 A1 | 5/2009 | Moffitt et al. |
| 2009/0248123 A1 | 10/2009 | Daniels et al. |
| 2009/0275997 A1 | 11/2009 | Faltys et al. |
| 2009/0276022 A1 | 11/2009 | Burnes et al. |
| 2009/0276023 A1 | 11/2009 | Morris et al. |
| 2009/0276025 A1 | 11/2009 | Burnes et al. |

FOREIGN PATENT DOCUMENTS

| | | |
|---|---|---|
| EP | 0 972 538 A2 | 1/2000 |
| WO | 00/13743 A1 | 3/2000 |
| WO | 03/086532 A1 | 10/2003 |
| WO | 2004/012809 A1 | 2/2004 |
| WO | 2004/054655 A1 | 7/2004 |
| WO | 2005/028023 A1 | 3/2005 |
| WO | 2007/083108 A2 | 7/2007 |
| WO | 2007/092330 A1 | 8/2007 |
| WO | 2007/146060 A2 | 12/2007 |
| WO | 2008024524 A1 | 2/2008 |
| WO | 2008/070120 A2 | 6/2008 |
| WO | 2008/094789 A1 | 8/2008 |
| WO | 2008/094952 A2 | 8/2008 |
| WO | 2008/153726 A2 | 12/2008 |
| WO | 2009/135082 A1 | 11/2009 |
| WO | 2009/148941 A1 | 12/2009 |

* cited by examiner

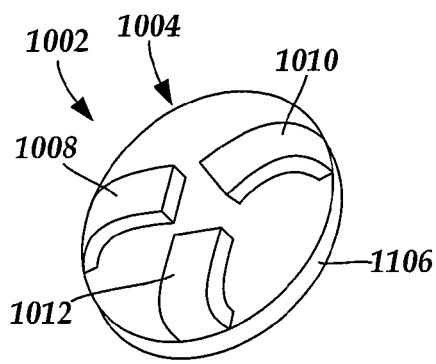 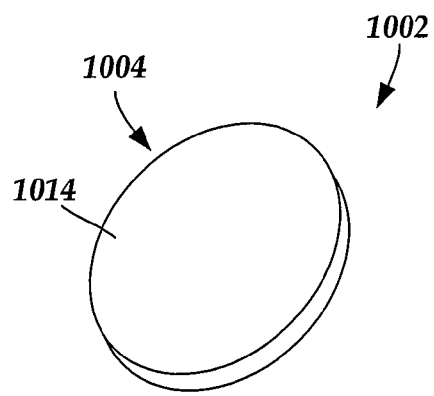
Fig. 10A                   Fig. 10B
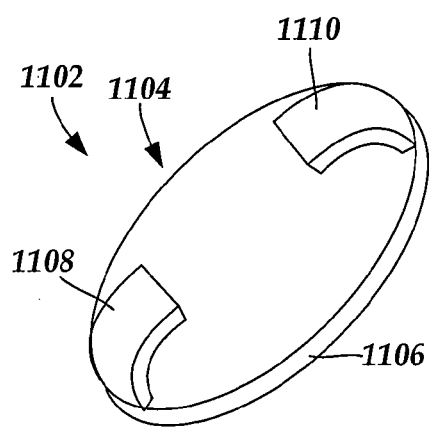 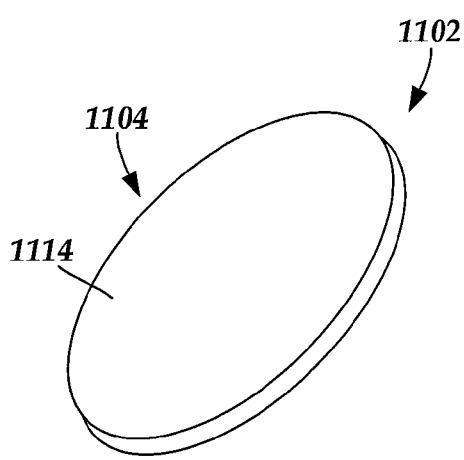
Fig. 11A                   Fig. 11B
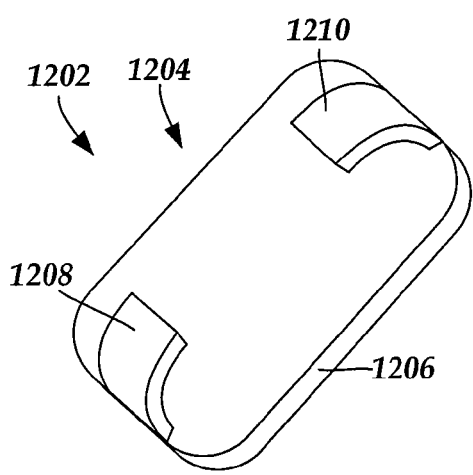 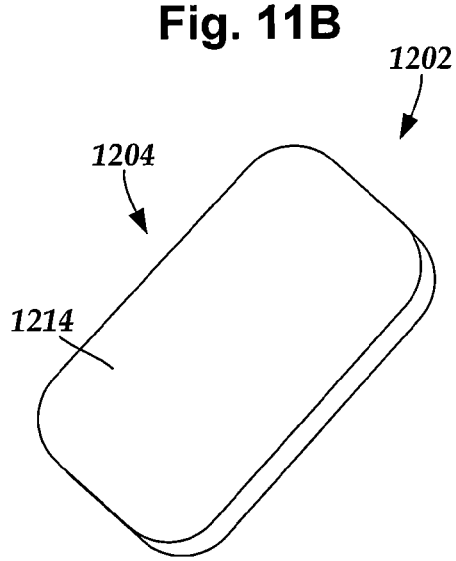
Fig. 12A                   Fig. 12B

ELECTRODE DESIGN FOR LEADS OF IMPLANTABLE ELECTRIC STIMULATION SYSTEMS AND METHODS OF MAKING AND USING

CROSS-REFERENCE TO RELATED APPLICATIONS

This application is a utility patent application based on a previously filed U.S. Provisional Patent Application Ser. No. 61/103,996 filed on Oct. 9, 2008, the benefit of which is hereby claimed under 35 U.S.C. §119(e) and incorporated herein by reference.

TECHNICAL FIELD

The present invention is directed to the area of implantable electrical stimulation systems and methods of making and using the systems. The present invention is also directed to implantable electrical stimulation systems having leads with electrodes capable of being disposed on lead surfaces more closely together than conventional electrodes, as well as methods of making and using the leads and implantable electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead includes a lead body with a distal end and a proximal end. A plurality of terminals are disposed at the proximal end of the lead body. A plurality of electrodes are disposed at the distal end of the lead body. Each electrode includes an electrode body and at least one anchoring member. The at least one anchoring member couples to the electrode body and extends into the lead body and beneath the electrode body to anchor the electrode to the lead body. A plurality of conductive wires electrically couple the plurality of electrodes to the plurality of terminals.

In another embodiment, an electrical stimulating system includes a lead body with a distal end and a proximal end, a control module configured and arranged to electrically couple to the proximal end of the lead body, and a connector for receiving the lead body. A plurality of terminals are disposed at the proximal end of the lead body. A plurality of electrodes are disposed at the distal end of the lead body. Each electrode includes an electrode body and at least one anchoring member. The at least one anchoring member couples to the electrode body and extends into the lead body and beneath the electrode body to anchor the electrode to the lead body. A plurality of conductive wires electrically couple the plurality of electrodes to the plurality of terminals. The control module includes a housing and an electronic subassembly disposed in the housing. The connector has a proximal end, a distal end, and a longitudinal length. The connector is configured and arranged to receive the lead body. The connector includes a connector housing and a plurality of connector contacts disposed in the connector housing. The connector housing defines a port at the distal end of the connector and is configured and arranged for receiving the proximal end of the lead body. The connector contacts are configured and arranged to couple to at least one of the plurality of terminals disposed on the proximal end of the lead body.

In yet another embodiment, a method for forming a lead includes placing a plurality of electrodes with electrode bodies into an arrangement so that the electrode bodies of the electrodes are separated from one another. Each electrode includes an electrode body and at least one anchoring member extending beneath the electrode body. A lead body is formed around the plurality of electrodes so that the electrodes are disposed at a distal end of the lead body. The lead body is also formed between two or more anchoring members of each electrode. Each of the plurality of electrodes is electrically coupled to a plurality of terminals disposed on a proximal end of the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 10A is a schematic perspective view of one embodiment of a bottom side of an electrode that includes a circular electrode body and three inwardly-bending anchoring members, according to the invention;

FIG. 10B is a schematic perspective view of one embodiment of a top side of the electrode shown in FIG. 10A, the electrode including a circular electrode body with an exterior surface, according to the invention;

FIG. 11A is a schematic perspective view of one embodiment of a bottom side of an electrode that includes a ovoid electrode body and two inwardly-bending anchoring members, according to the invention;

FIG. 11B is a schematic perspective view of one embodiment of a top side of the electrode shown in FIG. 11A, the electrode including an ovoid electrode body with an exterior surface, according to the invention;

FIG. 12A is a schematic perspective view of one embodiment of a bottom side of an electrode that includes a rounded rectangular electrode body and two inwardly-bending anchoring members, according to the invention;

FIG. 12B is a schematic perspective view of one embodiment of a top side of the electrode shown in FIG. 12A, the electrode including a rounded rectangular electrode body with an exterior surface, according to the invention;

DETAILED DESCRIPTION

The present invention is directed to the area of implantable electrical stimulation systems and methods of making and using the systems. The present invention is also directed to implantable electrical stimulation systems having leads with electrodes capable of being disposed on lead surfaces more closely together than conventional electrodes, as well as methods of making and using the leads and implantable electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741, 892; and U.S. patent application Ser. Nos. 10/353,101, 10/503,281, 11/238,240; 11/319,291; 11/327,880; 11/375, 638; 11/393,991; 11/609,586; and 11/396,309, all of which are incorporated by reference.

Figure 1:
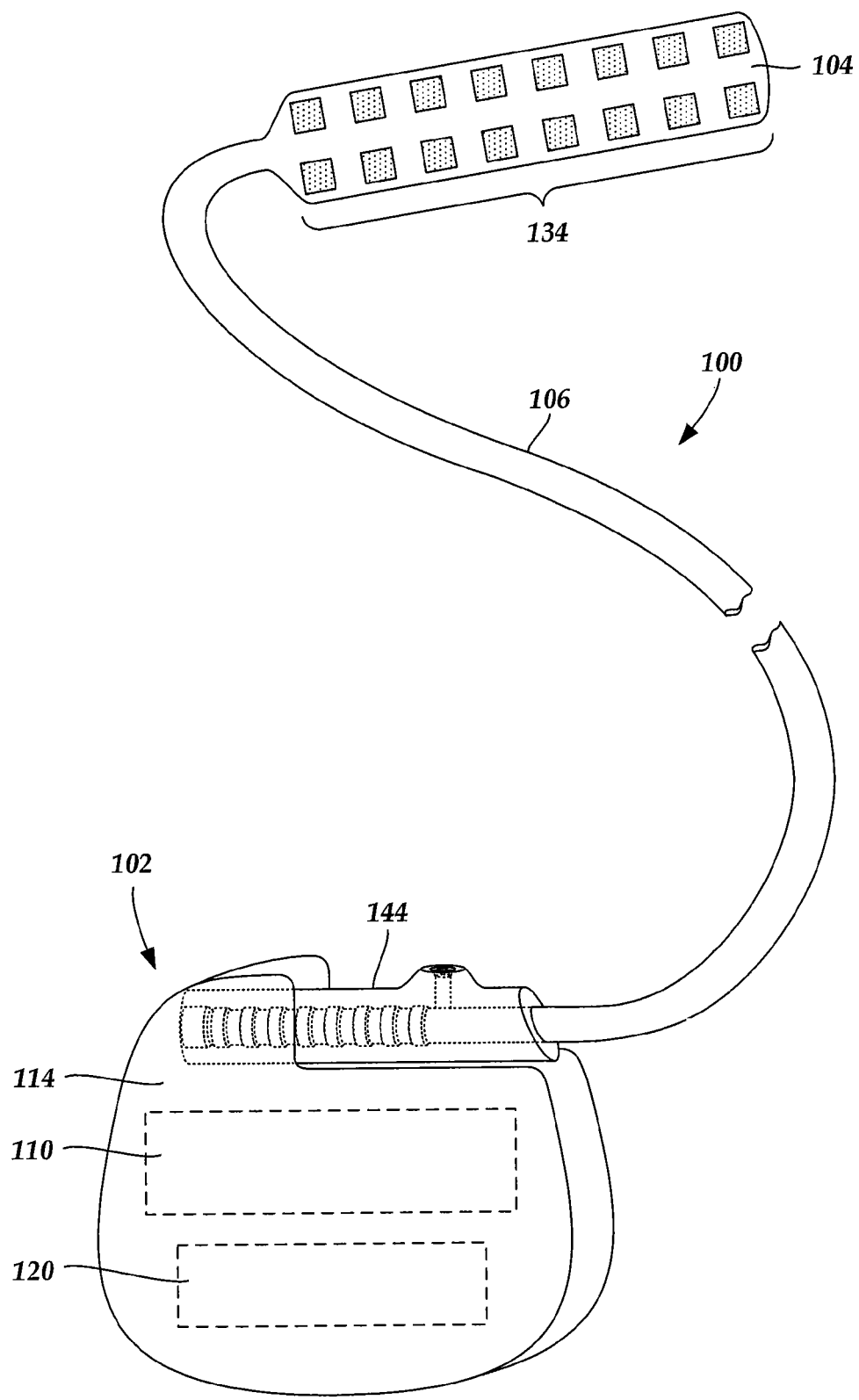
FIG. 1 is a schematic view of one embodiment of an electrical stimulation system, according to the invention.
Figure 2:
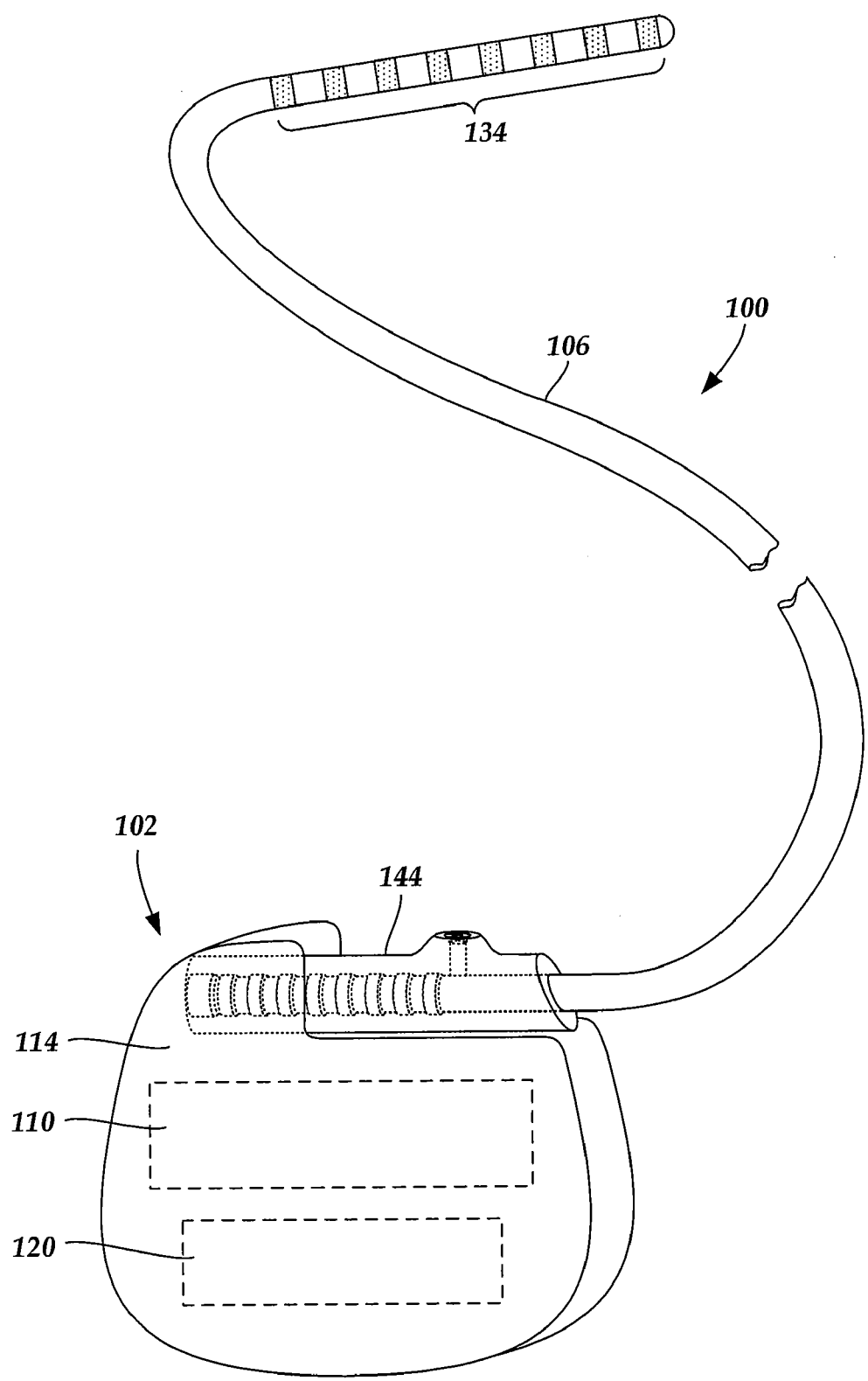
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead into a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
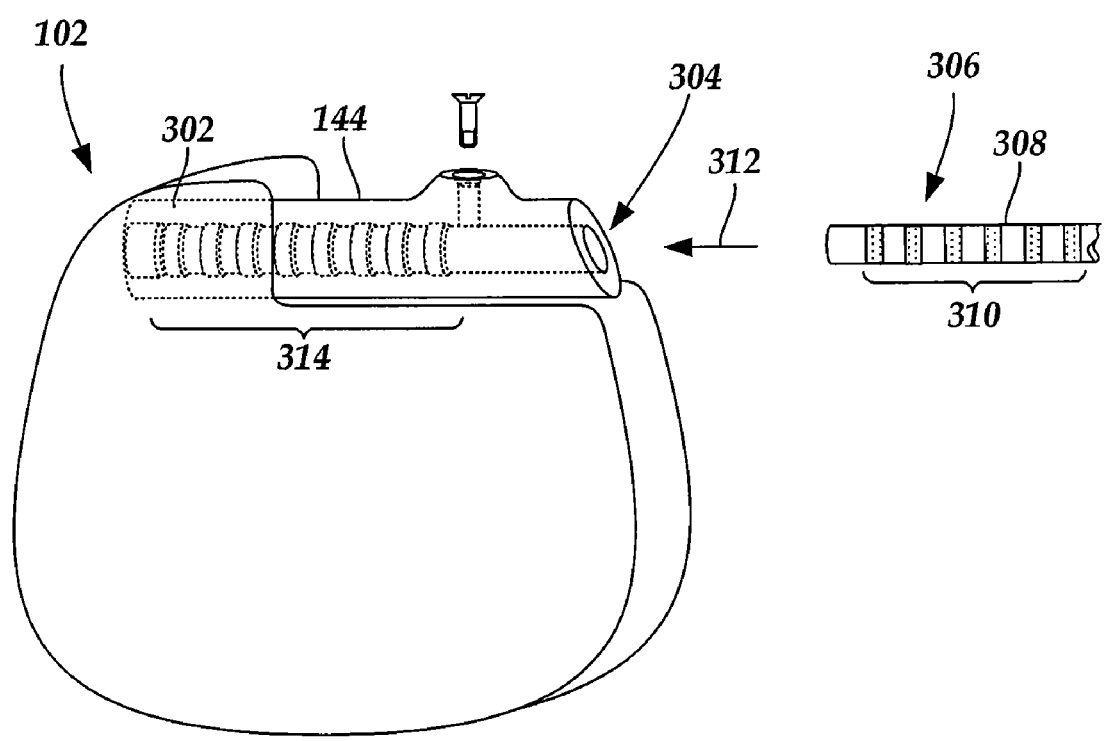
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
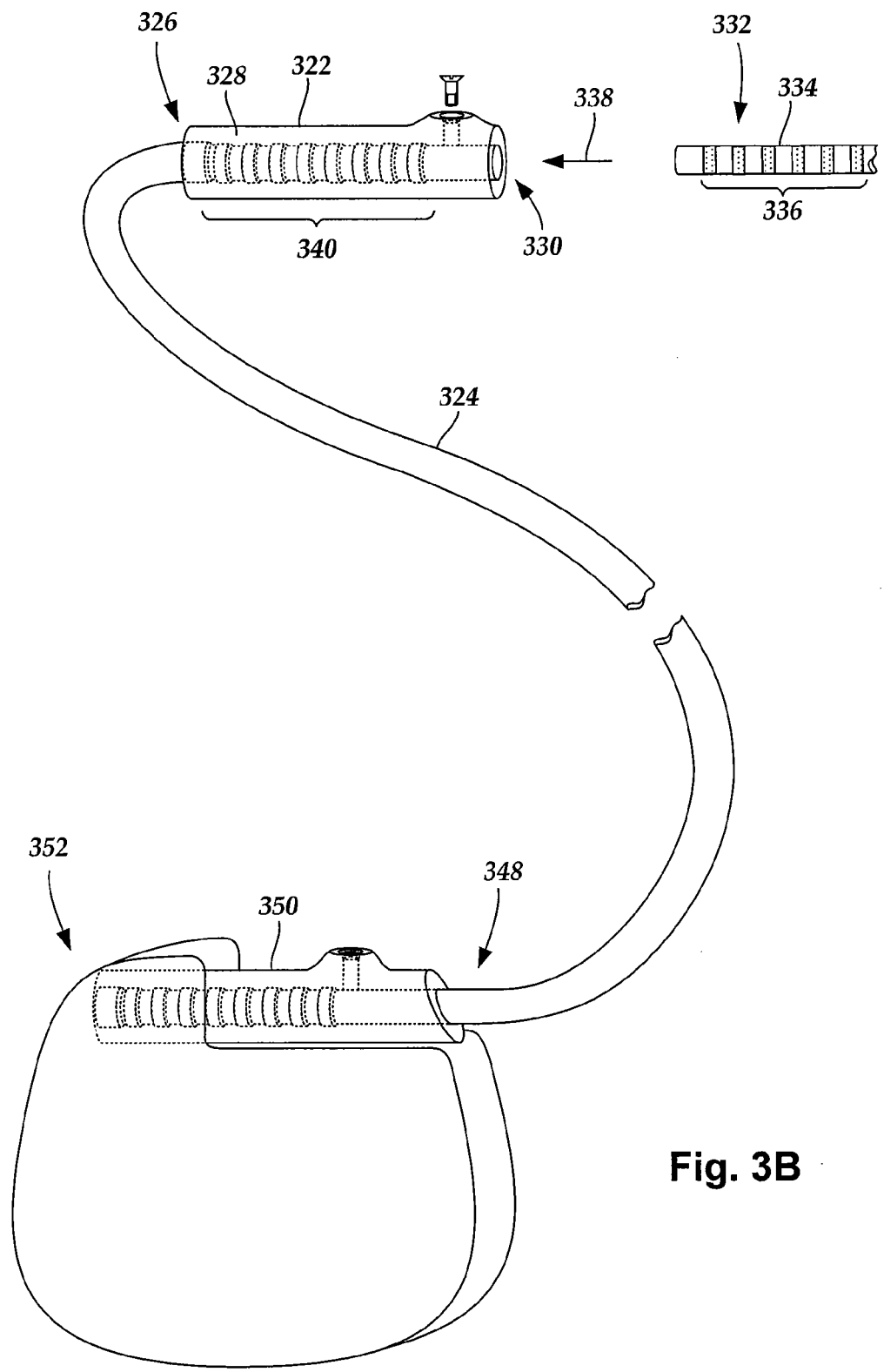
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Electrodes are generally positioned along the surface of a lead body in a selected arrangement (see e.g., FIG. 1). The electrodes may be held in place, at least in part, by one or more anchoring wings extending from the electrode into the lead body. Electrodes disposed on a lead are typically disposed some minimum distance apart from one another to prevent interactions between adjacent electrodes. For example, physical interference or short circuiting may occur when two electrodes physically contact one another, or even when the two electrodes come within a certain distance of one another.

For conventional electrodes, the anchoring wings generally extend outwardly from the electrode body some distance in a direction often approximately parallel to the surface of the lead body. Accordingly, the minimum distance that adjacent electrodes need to be spaced apart from one another, as measured from a center of one electrode to the center of an adjacent electrode ("center-to-center distance"), may be dictated by the distance that one or more anchoring wings outwardly extend from adjacent electrodes.

It may be an advantage to reduce the center-to-center distance between adjacent electrodes so that electrodes may be positioned more closely to one another on a lead. In at least some embodiments, reducing the center-to-center distance between adjacent electrodes may allow leads to be formed with increased electrode density from conventional leads and may also allow leads to be formed in sizes that are smaller than conventionally-sized leads. Employing electrical stimulation systems with leads with an increased electrode density may make it possible to target patient tissue more precisely. Increased stimulation precision may be especially beneficial for certain types of stimulation, for example, spinal cord stimulation, cortical stimulation, peripheral nerve stimulation, deep brain stimulation, cavernous-nerve stimulation, pudental-nerve stimulation, and the like.

In at least some embodiments, electrodes are described that each include an electrode body that may be anchored to a lead body by one or more anchoring members that extend beneath the electrode body. Consequently, in at least some embodiments, when a plurality of electrodes with anchoring members are arranged along the surface of a lead body, the electrodes may be spaced apart from one another such that the minimum center-to-center distance between the adjacent electrodes is determined by the size of the electrode bodies, not the size of the anchoring wings.

Figure 4:
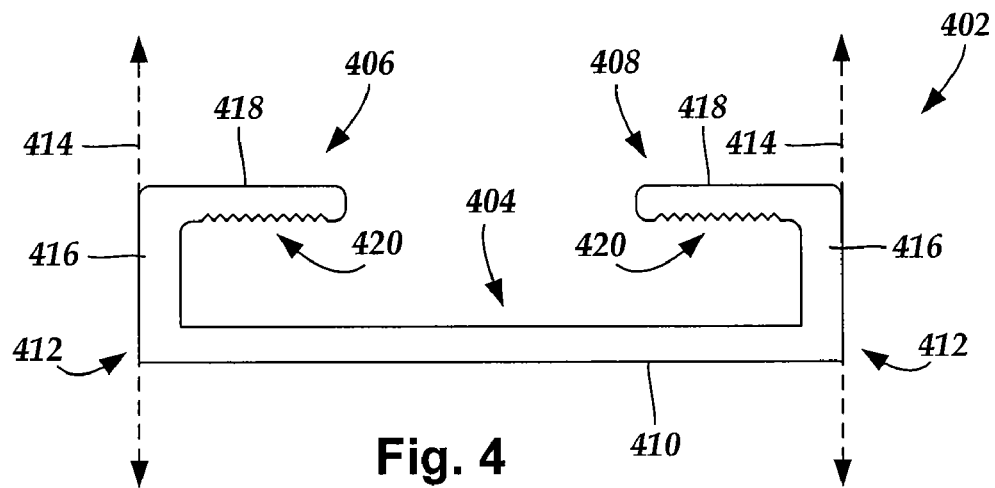
FIG. 4 is a schematic longitudinal cross-sectional view of one embodiment of an electrode that includes an electrode body and inwardly-bending anchoring members, according to the invention.

FIG. 4 is a schematic side view of one embodiment of an electrode 402 that includes an electrode body 404 ("body") and anchoring members 406 and 408. The body 404 includes an exterior surface 410 and an outer rim 412 extending around the perimeter of the body 404. The outer rim 412 defines the outermost boundary of the electrode 402 in a direction 414, shown in FIG. 4 as dashed lines with two-headed arrows. In at least some embodiments, the body 404 is substantially flat. In other embodiments, the body 404 is arced.

The anchoring members 406 and 408 include proximal regions 416 and distal regions 418. In at least some embodiments, the anchoring members 406 and 408 extend from the body 404 along the outer rim 412. In other embodiments, the anchoring members 406 and 408 extend from the body 404 towards the center of the body 404. In at least some embodiments, at least one of the proximal regions extends from the body 404 in a direction that is approximately perpendicular to the body 404. In at least some embodiments, at least one of the distal regions extends from the body 404 in a direction that is approximately parallel to the body 404. In at least some embodiments, at least one of the anchoring members 406 and 408 includes one or more securing elements 420 for increasing the anchoring ability of the anchoring member 406 and 408. In some embodiments, the securing element 420 includes one or more teeth.

In FIG. 4, the two-headed arrows showing the direction 414 are shown positioned at two ends of the outer rim 412. As shown in FIG. 4, the anchoring members 406 and 408 do not extend laterally beyond the boundary of the outer rim 412. In at least some embodiments, the direction 414 is approximately perpendicular to the body 404. In at least some embodiments, the exterior surface 410 is substantially flat. In other embodiments, the exterior surface 410 is substantially flat (see e.g., FIG. 14). In some embodiments, the electrode 402 may be formed as a unitary structure. In other embodiments, the body 404 may be formed separately from the one or more anchoring members 406 and 408 and subsequently coupled together.

The number of anchoring members 406 and 408 may vary. For example, there may be one, two, three, four, five, six, seven, eight, nine, ten, or more anchoring members 406 and 408. It will be understood that other numbers of anchoring members 406 and 408 may be used as well. The body 404 of the electrode 402 may be formed in many different shapes including, for example, circular, ovoid, triangular, rectangular, pentagonal, hexagonal, heptagonal, octagonal, nonagonal, decagonal, and the like. It will be understood that other body 404 shapes of may be used as well, including both regular and irregular shapes.

Figure 5:
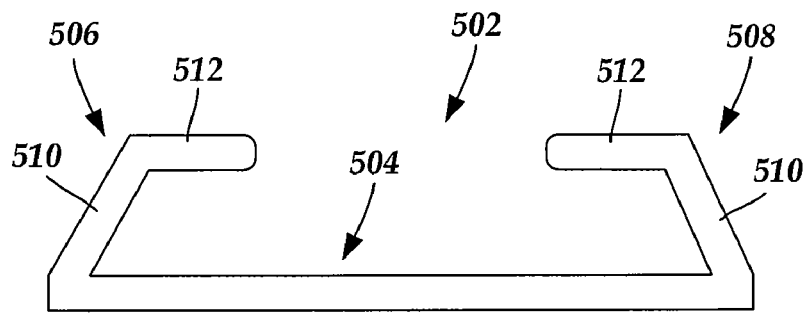
FIG. 5 is a schematic longitudinal cross-sectional view of a second embodiment of an electrode that includes an electrode body and inwardly-bending anchoring members, according to the invention.

The anchoring members of electrodes may extend from the body in many different ways. FIG. 5 shows one embodiment of an electrode 502 with a body 504 and anchoring members 506 and 508. The anchoring members 506 and 508 include proximal regions 510 and distal regions 512. In FIG. 5, the proximal regions 510 are shown extending inwardly, towards a center of the body 504.

Figure 6:
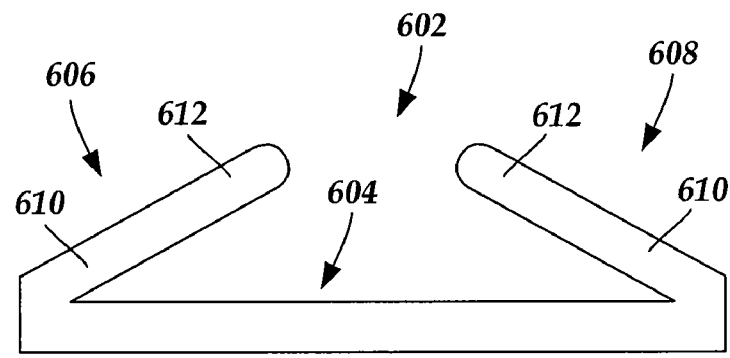
FIG. 6 is a schematic longitudinal cross-sectional view of a third embodiment of an electrode that includes an electrode body and inwardly-bending anchoring members, according to the invention.

FIG. 6 shows one embodiment of an electrode 602 with a body 604 and anchoring members 606 and 608. The anchoring members 606 and 608 include proximal regions 610 and distal regions 612. In FIG. 6, the proximal regions 610 and the distal ends are 612 are shown oriented in similar directions to one another, extending inwardly towards a center of the body 604. In at least some embodiments, when the proximal regions 510 and 610 extend inwardly, the distal regions 512 or 612 may extend outwardly without extending beyond the outer rim (412 in FIG. 4).

Figure 7:
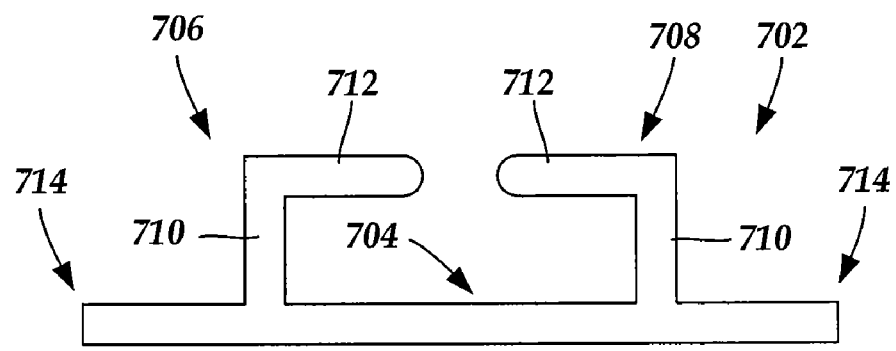
FIG. 7 is a schematic longitudinal cross-sectional view of a fourth embodiment of an electrode that includes an electrode body and inwardly-bending anchoring members extending from locations interior of the outer rim, according to the invention.

FIG. 7 shows one embodiment of an electrode 702 with a body 704 and anchoring members 706 and 708. The anchoring members 706 and 708 include proximal regions 710 and distal regions 712. In FIG. 7, the proximal regions 710 extend from the body 704 from a location medial to the outer rim 714 and the distal regions 712 extend inwardly towards a center of the body 704.

Figure 8:
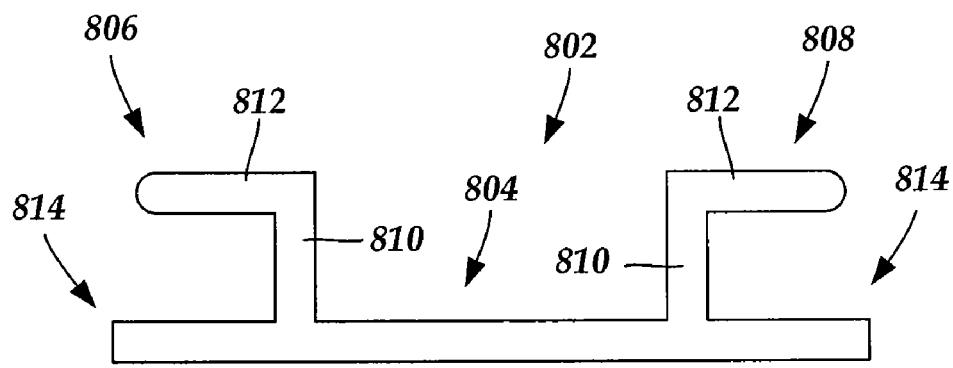
FIG. 8 is a schematic longitudinal cross-sectional view of a fifth embodiment of an electrode that includes an electrode body and outwardly-bending anchoring members extending from locations interior of the outer rim, according to the invention.

FIG. 8 shows one embodiment of an electrode 802 with a body 804 and anchoring members 806 and 808. The anchoring members 806 and 808 include proximal regions 810 and distal regions 812. In FIG. 8, the proximal regions 810 extend from the body 804 from a location medial to the outer rim 814 and the distal regions 812 extend outwardly towards the outer rim 814, without extending beyond the outer rim 814.

Figure 9A:
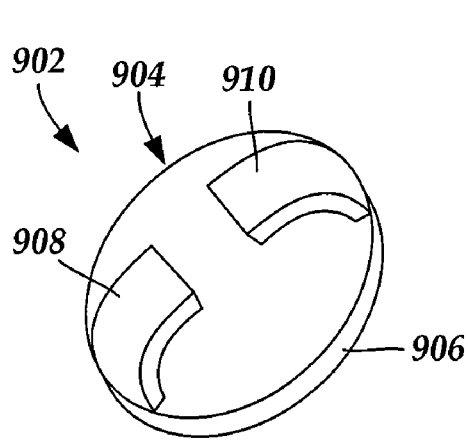
FIG. 9A is a schematic perspective view of one embodiment of a bottom side of an electrode that includes a circular electrode body and two inwardly-bending anchoring members, according to the invention.
Figure 9B:
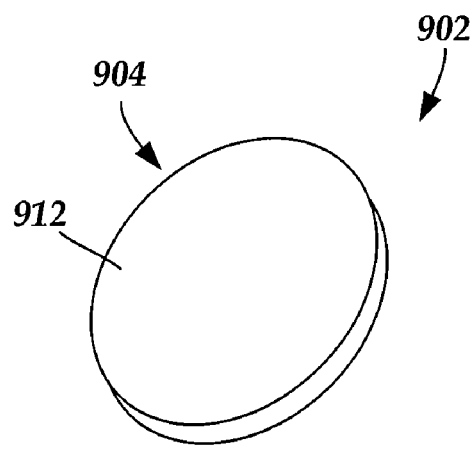
FIG. 9B is a schematic perspective view of one embodiment of a top side of the electrode shown in FIG. 9A, the electrode including a circular electrode body with an exterior surface, according to the invention.

Many different numbers of anchoring members may extend from the body. FIG. 9A is a schematic perspective view of one embodiment of a bottom side of an electrode 902 that includes a circular body 904 with an outer rim 906 and two anchoring members 908 and 910. FIG. 9B is a schematic perspective view of one embodiment of a top side of the electrode 902. The electrode 902 includes the circular body 904 with an exterior surface 912. FIG. 10A is a schematic perspective view of one embodiment of an electrode 1002 that includes a circular body 1004 with an outer rim 1006 and three anchoring members 1008, 1010, and 1012. FIG. 10B is a schematic perspective view of one embodiment of a top side of the electrode 1002. The electrode 1002 includes the circular body 804 with an exterior surface 814.

An electrode body may be many different shapes. In at least some embodiments, the electrode has an ovoid shape. FIG. 11A is a schematic perspective view of one embodiment of a bottom side of an electrode 1102 that includes an ovoid body 1104 with an outer rim 1106 and two anchoring members 1108 and 1110. FIG. 11B is a schematic perspective view of one embodiment of a top side of the electrode 1102. The electrode 1102 includes the ovoid body 1104 with an exterior surface 1114. FIG. 12A is a schematic perspective view of one embodiment of a bottom side of an electrode 1202 that includes a rounded rectangular body 1204 with an outer rim 1206 and two anchoring members 1208 and 1210. FIG. 12B is a schematic perspective view of one embodiment of a top side of the electrode 1202. The electrode 1202 includes the rounded rectangular body 1204 with an exterior surface 1214. It will be understood that an electrode body may have many other shapes, as well.

Figure 13A:
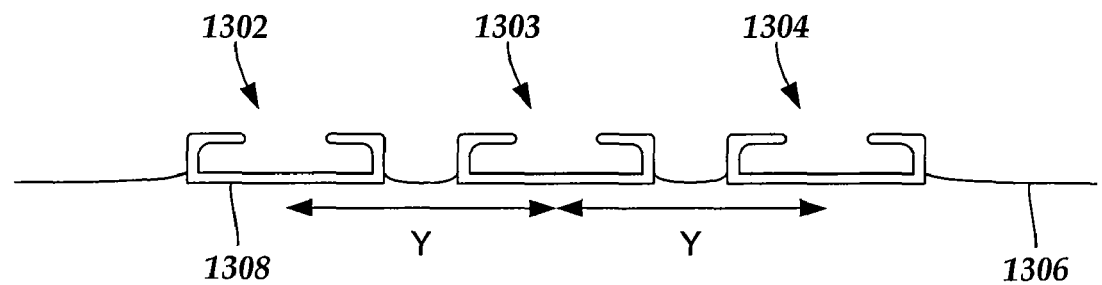
FIG. 13A is a schematic longitudinal cross-sectional view of one embodiment of three adjacent electrodes, each electrode including an electrode body and anchoring members, the electrodes each anchored to a lead body by the anchoring members so that an exterior portion of each electrode body is flush with the surface of the lead body, according to the invention.
Figure 13B:
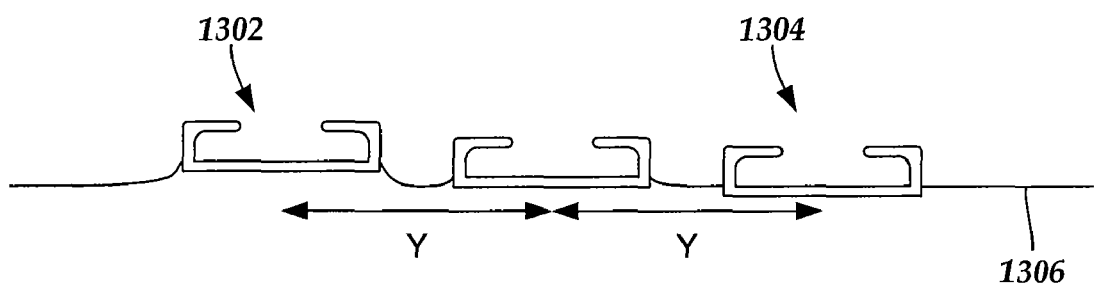
FIG. 13B is a schematic longitudinal cross-sectional view of one embodiment of the electrodes shown in FIG. 13A with an exterior portion of one of the electrodes being inset from a lead body, another being flush with the lead body, and another protruding from the lead body, according to the invention.

FIG. 13A is a schematic longitudinal cross-sectional view of one embodiment of three adjacent electrodes 1302-1304 anchored to a lead body 1306. The electrodes 1302-1304 each include an exterior surface, such as exterior surface 1308. In at least some embodiments, the exterior surface of at least one of the electrodes 1302-1304 is substantially flat and extends in a direction that is parallel with the surface of the lead body 1306. In at least some embodiments, the exterior surface of at least one of the electrodes 1302-1304 is approximately flush with the surface of the lead body 1306 (as shown by each of the electrodes 1302-1304 in FIG. 13A). In at least some embodiments, the exterior surface of at least one of the electrodes may be inset from the surface of the lead body 1306, as shown by electrode 1302 in FIG. 13B. In at least some embodiments, the exterior surface of at least one of the electrodes may protrude from the surface of the lead body 1306, as shown by electrode 1304 of FIG. 13B.

In at least some embodiments, the electrodes 1302-1304 are disposed on the lead body 1306 a center-to-center distance "Y" apart from one another. In at least some embodiments, the center-to-center distance "Y" is less than the center-to-center distance achievable with a comparably-sized electrode with outwardly-extending anchoring wings. In at least some embodiments, the center-to-center distance "Y" is approximately half the center-to-center distance achievable with a comparably-sized electrode with outwardly-extending anchoring wings. In at least some embodiments, the minimum distance "Y" is approximately one-fourth the center-to-center distance achievable with a comparably-sized electrode with outwardly-extending anchoring wings.

Figure 14:
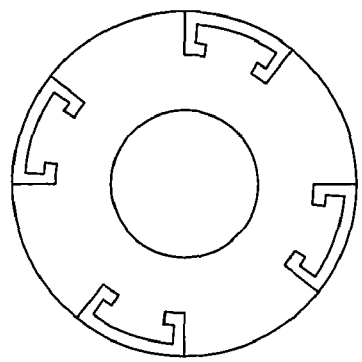
FIG. 14 is a schematic transverse cross-sectional view of one embodiment of four electrodes with arced bodies radially disposed in a segmented arrangement on a lead, according to the invention.

As mentioned above, with reference to FIG. 4, electrodes may have an arced body. In at least some embodiments, the curvature of an arced body is configured and arranged so that the exterior surface of the electrode has a similar curvature to a similarly-sized arc on the surface of the lead body. FIG. 14 is a schematic transverse cross-sectional view of one embodiment of four electrodes with arced bodies radially disposed in a segmented arrangement on a lead.

Figure 15:
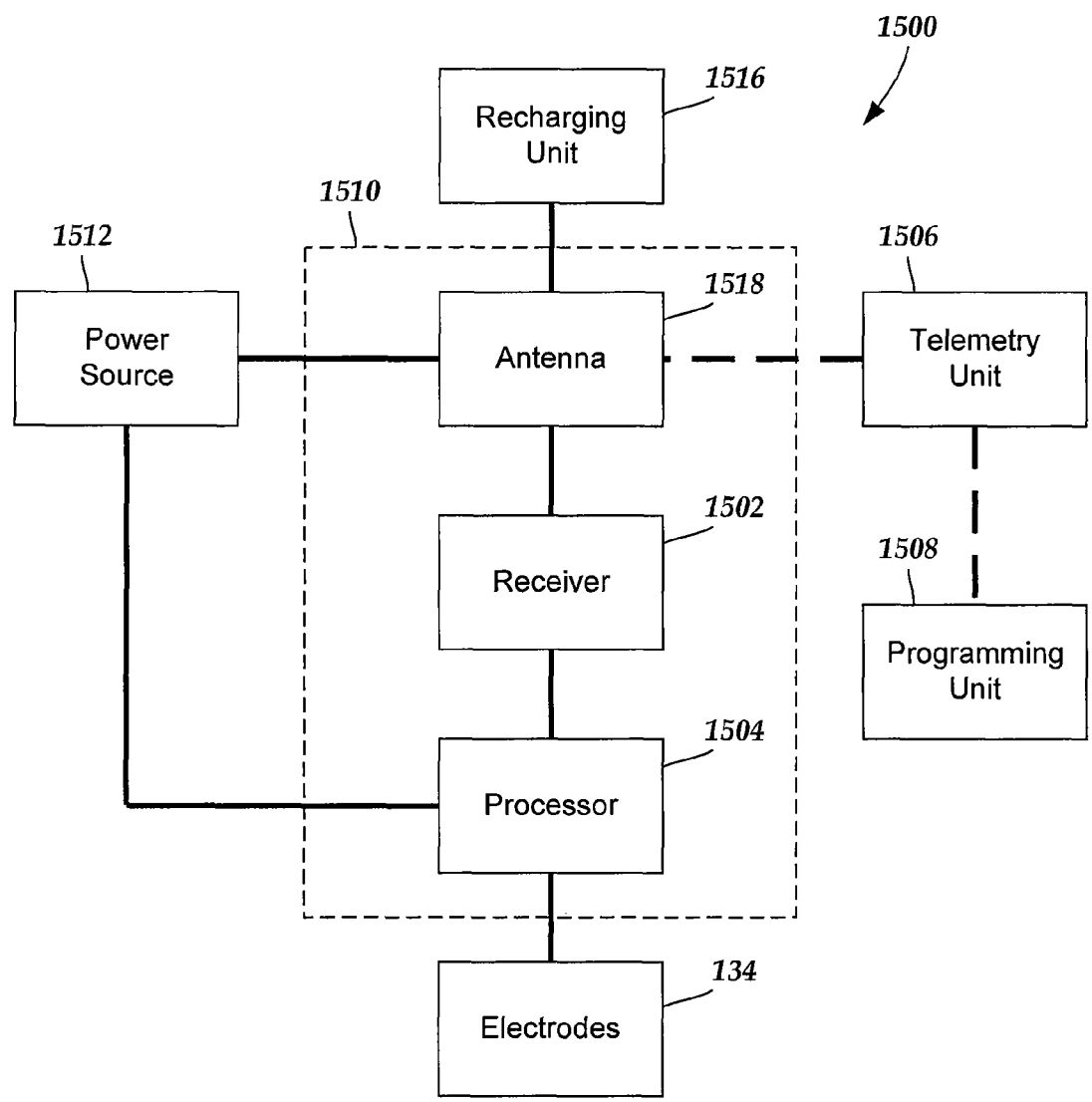
FIG. 15 is a schematic overview of one embodiment of components of a stimulation system, including an electronic subassembly disposed within a control module, according to the invention.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, power source 1512, antenna 1518, receiver 1502, and processor 1504) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna to a recharging unit 1516 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 may select which electrode(s) are cathodes and which electrode(s) are anodes. In some embodiments, the processor 1504 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by a programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include an antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 1504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead comprising:
  a lead body with a distal end and a proximal end;
  a plurality of terminals disposed along the proximal end of the lead body;
  a plurality of electrodes disposed along the distal end of the lead body, each electrode comprising an electrode body, an outer rim extending around a perimeter of the electrode body, at least one anchoring member coupled to the electrode body and extending into the lead body and beneath the electrode body to anchor the electrode to the lead body, the at least one anchoring member comprising a proximal region coupled to the electrode body and an opposing distal region configured and arranged for anchoring the electrode body to the lead body, and one or more teeth disposed along the distal region of the at least one anchoring member, the one or more teeth configured and arranged for facilitating anchoring of the electrode body to the lead body; and a plurality of conductive wires electrically coupling the plurality of electrodes to the plurality of terminals.

2. The lead of claim 1, wherein a surface of the electrode body is flush with a surface of the lead body.

3. The lead of claim 1, wherein a surface of the electrode body is inset from a surface of the lead body.

4. The lead of claim 1, wherein a surface of the electrode body protrudes from a surface of the lead body.

5. The lead of claim 1, wherein at least one of the proximal region or the distal region of the at least one anchoring member bends inwardly towards a center of the electrode body.

6. The lead of claim 1, wherein the proximal region of the at least one anchoring member extends in a direction that is perpendicular to a surface of the lead body.

7. The lead of claim 1, wherein the distal region of the at least one anchoring member extends in a direction that is parallel to a surface of the lead body.

8. The lead of claim 1, wherein the proximal region of the at least one anchoring member extends inwardly towards a center of the electrode body.

9. The lead of claim 1, wherein the electrode body is one of round or ovoid.

10. An electrical stimulating system comprising:
the lead of claim 1;
a control module configured and arranged to electrically couple to the proximal end of the lead body, the control module comprising
a housing, and
an electronic subassembly disposed in the housing; and
a connector having a proximal end, a distal end, and a longitudinal length, the connector configured and arranged to receive the lead body, the connector comprising
a connector housing defining a port at the distal end of the connector, the port configured and arranged for receiving the proximal end of the lead body, and
a plurality of connector contacts disposed in the connector housing, the connector contacts configured and arranged to couple to at least one of the plurality of terminals disposed on the proximal end of the lead body.

11. The electrical stimulating system of claim 10, wherein the connector is disposed on the control module.

12. The electrical stimulating system of claim 10, further including a lead extension having a distal end and at least one proximal end, the connector disposed on the distal end of the lead extension.

13. The electrical stimulating system of claim 12, wherein at least one of the proximal ends of the lead extension is configured and arranged for insertion into another connector.

14. The electrical stimulating system of claim 12, wherein at least one of the proximal region or the distal region of the at least one anchoring member bends inwardly towards a center of the electrode body.

15. A lead comprising:
a lead body with a distal end and a proximal end;
a plurality of terminals disposed at the proximal end of the lead body;
a plurality of electrodes disposed at the distal end of the lead body, each electrode comprising
an electrode body having a first major surface and an opposing second major surface,
an outer rim extending around a perimeter of the electrode body, and
a plurality of anchoring members coupled to the second major surface of the electrode body and extending into the lead body and beneath the electrode body to anchor the electrode to the lead body, the plurality of anchoring members each comprising a proximal region coupled to the electrode body and an opposing distal region configured and arranged for anchoring the electrode body to the lead body; and
a plurality of conductive wires electrically coupling the plurality of electrodes to the plurality of terminals;
wherein for each anchoring member of the plurality of anchoring members the proximal region of the anchoring member couples to the electrode body from a location medial to the outer rim;
wherein one or more teeth are disposed along the distal region of at least one anchoring member of the plurality of anchoring members.

16. The lead of claim 15, wherein for at least one anchoring member of the plurality of anchoring members the distal region extends inwardly towards a center of the electrode body.

17. The lead of claim 15, wherein for at least one anchoring member of the plurality of anchoring members the distal region extends outwardly towards the outer rim.

18. The lead of claim 15, wherein for at least one anchoring member of the plurality of anchoring members the distal region extends outwardly towards the outer rim without extending beyond the outer rim.

19. The lead of claim 15, wherein the first major surface is arced.

20. The lead of claim 15, wherein the first major surface of the electrode body is flush with an outer surface of the lead body.

* * * * *